United States Patent
Huang et al.

(10) Patent No.: US 8,415,384 B2
(45) Date of Patent: Apr. 9, 2013

(54) REDUCING MYOCARDIAL REPERFUSION INJURY BY THE COMBINATION THERAPY OF PROTEIN KINASE A ACTIVATION AND B1-ADRENERGIC RECEPTOR BLOCKADE

(75) Inventors: Ming-He Huang, League City, TX (US); Kenichi Fujise, Galveston, TX (US); Barry F. Uretsky, Fort Smith, AR (US)

(73) Assignee: The Board of Regents of the University of Texas System, Austin, TX (US)

(*) Notice: Subject to any disclaimer, the term of this patent is extended or adjusted under 35 U.S.C. 154(b) by 0 days.

(21) Appl. No.: 12/997,485

(22) PCT Filed: Jun. 12, 2009

(86) PCT No.: PCT/US2009/047181
§ 371 (c)(1),
(2), (4) Date: Feb. 28, 2011

(87) PCT Pub. No.: WO2009/152415
PCT Pub. Date: Dec. 17, 2009

(65) Prior Publication Data
US 2011/0190206 A1    Aug. 4, 2011

Related U.S. Application Data

(60) Provisional application No. 61/060,992, filed on Jun. 12, 2008.

(51) Int. Cl.
*A61K 31/44* (2006.01)
*A61K 31/675* (2006.01)
*A61K 31/135* (2006.01)
*A61P 9/10* (2006.01)

(52) U.S. Cl. ........... 514/352; 514/94; 514/651; 514/824

(58) Field of Classification Search .................. None
See application file for complete search history.

(56) References Cited

FOREIGN PATENT DOCUMENTS

| | | |
|---|---|---|
| DE | EP 1579862 A | 9/2005 |
| WO | WO 2005/037230 A | 4/2005 |
| WO | WO 2008/134727 A | 11/2008 |

OTHER PUBLICATIONS

Record for Clinical Trial NCT00348101, dated May 29, 2007, "Effects of Beta-Blocker Therapy and Phosphodiesterase Inhibition on Cardiac Neurohormonal Activation", no author listed, 4 pages as printed.*
Huang et al, 2011. Cardiovasc Drugs Ther. 25: 223-232.*
Phillips, J Pharm Pharmacology 53: 1169-1174, 2001.*
Vidal et al. 2005. European Journal of Cancer. 41: 2812-2818.*
Pirollo et al, 2008. Cancer Res. 68(5): 1247-1250.*

(Continued)

*Primary Examiner* — Zachary Howard
(74) *Attorney, Agent, or Firm* — Landrum Intellectual Property

(57) ABSTRACT

Embodiments of the invention are directed to methods of treating reperfusion or resuscitation injury in an individual in need of such treatment, comprising the step of administering to the individual who has had, having, or is at immediate risk of having an ischemic event an amount of a composition comprising a protein kinase A (PKA) activator and a $\beta_1$-adrenergic receptor antagonist sufficient to reduce reperfusion injury to an ischemic tissue.

8 Claims, 4 Drawing Sheets

OTHER PUBLICATIONS

Boldt, Joachim, et al., "Combined use of ultra-short acting beta-blocker esmolol and intravenous phosphodiesterase 3 inhibitor enoximone", Expert Opinion, 2007, pp. 2135-2147, vol. 8(13).

Hauptman, Paul J., et al., "Novel Use of a Short-Acting Intravenous Beta Blocker in Combination with Inotropic Therapy as a Bridge to Chronic Oral Beat Blockade in Patients with Advanced Heart Failure", Clin. Cardiol., 2002, pp. 247-249, vol. 25.

International Preliminary Report on Patentability, PCT/US2009/047181, International filing date Jun. 12, 2009, IPR issued Dec. 14, 2010.

Sidi, A., et al., "Treatment of ischaemic left ventricular dysfunction with milrinone or dobutamine administered during coronary artery stenosis in the presence of beta blockade in pigs", British Journal of Anaesthesia, Dec. 1, 2006, pp. 799-807, vol. 96(6).

Sidi, A., et al., "Administration of milrinone before ischemia, in the presence of beta-blockade, to treat metabolic impairment and myocardial stunning in pigs", Acta Anaesthesiol Scandinavica Foundation, 2008, pp. 397-405, vol. 52.

* cited by examiner

REDUCING MYOCARDIAL REPERFUSION INJURY BY THE COMBINATION THERAPY OF PROTEIN KINASE A ACTIVATION AND B1-ADRENERGIC RECEPTOR BLOCKADE

The present application is a national phase application under 35 U.S.C. §371 of International Application No. PCT/US2009/047181 filed Jun. 12, 2009 which claims benefit of priority to U. S. Provisional Application Ser. No. 61/060,992 filed Jun. 12, 2008, the entire contents of which are hereby incorporated by reference.

BACKGROUND OF THE INVENTION

A. Field of the Invention

Embodiments of this invention are directed generally to biology, medicine, and cardiology. In particular aspects, the invention is related to combination therapy for treating cardiac and cardiovascular disorders and conditions, such as reperfusion injury after acute myocardial infarction (MI).

B. Background

Currently, there are 5 million American with congestive heart failure, with nearly 500,000 new cases being diagnosed every year. Because of the direct costs of care for heart failure, estimated at $10 billion to $38 billion per year, the Centers for Medicare and Medicaid Services targeted heart failure as the disease most worthy of cost-effective management. Improvement in heart failure treatment in terms of innovative pharmacological strategies is urgently needed in this heart failure epidemic era.

In addition, acute myocardial infarction (MI) is the leading killer in the United States accounting for 54% mortality of total cardiovascular disease-related death (2004 NHLBI Chartbook). Although reperfusion therapy during acute MI with percutaneous coronary intervention (PCI) or thrombolysis salvages myocardium that would ultimately die without reperfusion, rapidly restoring blood flow to myocardium can also cause lethal injury to vulnerable myocardial cells (i.e., reperfusion injury). The restoration of blood flow can lethally compromise oxygen-deprived cells. Reperfusion injury may offset the optimal salvage of myocardium achieved by PCI and/or thrombolysis. Over the last 20 years extensive research efforts have been devoted to develop therapeutic strategies to prevent reperfusion injury.

There is a need for additional compositions and methods for the treatment of cardiac and cardiovascular disorders and myocardial reperfusion injury by limiting infarct-size through pharmacological post-ischemia conditioning reperfusion injury, and post-ischemia conditioning.

SUMMARY OF THE INVENTION

Reperfusion injury is an unresolved clinical problem associated with restoration of blood flow to an ischemic organ, such as during acute MI followed by reperfusion therapy. Ischemia is defined as the restriction in blood supply, generally due to factors in the blood vessels, with resultant damage or dysfunction of tissue. Unfortunately, there is no drug clinically available that can be given after the onset of acute MI for reducing reperfusion injury, particularly when reperfusion therapy, such as PCI will be performed. Mobilization and/or administration of compounds or endogenous cardioprotective neurohormones that activate Protein Kinase A (PKA) may provide a novel therapeutic strategy for treating and/or limiting reperfusion injury. In addition, administrating a PKA activator (e.g., milrinone) together with β1-adrenergic receptor antagonist further improves the infarct-size reducing and/or limiting effects of the PKA activators.

Intravenous infusion of a PKA activator such as milrinone (a phosphodiesterase inhibitor (PDI)) has only been used for temporary treatment of decompensated congestive heart failure symptoms, a condition distinct from repefusion injury or MI. Milrinone may temporarily improve hemodynamic state and relieve the symptoms, but, does not exert heart protection. On the contrary, long-term use of milrinone increases mortality in patients with congestive heart failure (Packer 1991). Recent clinical trials demonstrated that intravenous milrinone therapy causes more harm in heart failure patients with etiology of ischemic cardiomyopathy (i.e., heart failure caused by myocardial infarction). Milrinone-treated patients with ischemic etiology have worse outcomes than those treated with placebo in terms of the composite of death or rehospitalization (Felker 2003).

In a rat model, administration of milrinone before the onset of acute myocardial infarction confers subsequent infarct-size reduction (Sanada 2001), a heart protective phenomenon termed ischemia preconditioning. Ischemia postconditioning using milrinone has not been shown to protect the heart from reperfusion injury when it is given after the onset of acute myocardial infarction. As a matter of fact, in a canine model, administration of milrinone 30-min after the onset of acute myocardial infarction showed no infarct-size reduction (Campbell 1987). Thus, neither clinical trials nor experimental studies have demonstrated cardiac benefit of milrinone given to the patients who have had acute myocardial infarction or congestive heart failure due to ischemic cardiomyopathy.

Esmolol is an example of a $\beta_1$-adrenergic receptor antagonists (or β-blocker). It has been used for the treatment of cardiac arrhythmia. Although β-blockers have been used routinely in the treatment of acute myocardial infarction with clear benefit, it has been controversial with respect to whether β-blockers actually reduce infarct-size. While some clinical studies demonstrated infarct-size reduction by β-blockers (Anonymous 1986, Roque 1987), other trials failed to support such an effect (Rude 1986, Heber 1987, Van de Werf 1993, Ellis 2001). Similarly, inconsistent results regarding β-blocker-mediated infarct-size-reduction have been reported in animal models (Kudoh 1984). The present invention describes the benefits of a combination therapy comprising administration of a PKA activator and a β1 adrenergic receptor antagonists in treating, reducing, limiting, abrogating and preventing injury to tissue post-ischemia or during an ischemic or reperfusion event.

"Ischemia-preconditioning" is the most frequent experimental model for studying reperfusion injury (Murry, 1986), but translation to the clinical arena has been challenging. The broad definition of ischemia-precondition is that of mobilizing endogenous cardioprotective mechanisms by administering short periods of decreased oxygenation and/or drug prior to the onset of MI can reduce infarct size during the reperfusion period. The major problem of ischemia-preconditioning has been that to reduce infarct size the preconditioning event or drug requires institution hours to days prior to MI onset. Thus, ischemia-preconditioning is clinically unrealistic, since it is difficult to predict a MI and patients arrive at the hospital already experiencing a MI.

"Ischemia-postconditioning" is a new concept aimed at therapy that can be delivered at the beginning of reperfusion during an acute MI to reduce reperfusion-injury. Reperfusion can be initiated by artificial or natural processes. Artificial processes include mechanical reperfusion, chemical reperfusion, and the like. Mechanical reperfusion, for example, can be by angioplasty and other procedures utilizing an intravascular catheter. Chemical reperfusion includes, but is not limited to administration of thrombolytics, such as alterplase, anistreplace, reteplase, streptokinase, tenecteplase, and urokinase to name a few. Typically, administration of the compositions of the invention is typically intravascularly, intraosseusly, intraarterially, transdermally, transmucosally, or by inhalation. In certain aspects, the compositions of the invention are administered through the arteries supplying blood to a particular target tissue, e.g., a coronary artery. The composition can be administered intravascularly, intravenously, and/or intraarterially. In certain aspects, the compositions are administered by an intracoronary route. Currently, only percutaneous coronary catheter based strategy has shown clinical promise to achieve "mechanical" ischemia-postconditioning (Staat 2005, Vinten-Johansen 2005).

Certain embodiments of the invention are directed to methods of treating reperfusion or resuscitation injury in an individual in need of such treatment, comprising the step of administering to the individual who has had, having, or is at immediate risk of having an ischemic event an amount of a composition comprising a protein kinase A (PKA) activator and a $\beta_1$-adrenergic receptor antagonist sufficient to reduce reperfusion injury to an ischemic tissue.

Still further embodiments of invention are directed to methods of reducing or limiting myocardial infarct size in an individual in need of such treatment, comprising the step of administering to the individual a pharmacological effective amount of a composition comprising a PKA activator and/or a $\beta_1$-adrenergic receptor antagonist.

Yet a further embodiment are directed to methods of reducing drug-induced cardiomyopathy in an individual, comprising administering to the individual a pharmacological effective amount of a composition comprising a PKA activator and/or a $\beta_1$-adrenergic receptor antagonist. In certain aspects a composition is administered prior to and/or subsequent to the administration of the drug. Typically the drug is a chemotherapeutic agent, such as doxorubicin (Adriamycin) or daunorubicin (Cerubidine).

In certain aspects of the invention, reperfusion injury is tissue infarction. A PKA activator can be phosphodiesterase inhibitor, or $\beta_2$-adrenergic receptor agonist, or a composition comprising vasodilator and $\beta_2$-adrenergic receptor agonist. Phosphodiesterase inhibitors include, but is not limited to milrinone, enoximone, vinpocetine, erythro-9-(2-hydroxy-3-nonyl)adenine, mesembrine, rolipram, ibudilast, sildenafil, tadalafil, vardenafil, udenafil, or avanafil. In certain aspects, the phosphodiesterase inhibitor is milrinone.

$\beta_2$-adrenergic receptor agonist can include, but are not limited to terbutaline, albuterol, biterol, dobutamine, dopamine, epinephrine, formoterol, isoproterenol, levalbuterol, metaproterenol, salmeterol, or ritodrine. In certain aspects, the $\beta_2$-adrenergic receptor agonist is terbutaline. In still a further aspect, the $\beta_2$-adrenergic receptor agonist is terbutaline and the vasodilator is calcitonin gene-related peptide (CGRP) or a mimetic thereof. In certain aspects, the vasodilator is CGRP, adrenomedullin, or amylin. In a particular aspect the vasodilator is a CGRP receptor agonist.

Phosphodiesterase inhibitor can be administered at a dose of 0.01, 0.1, 0.5, 1, 1.5, 5, 10, 25, 50, 100, 500 mg/kg or mg/kg to 500, 600, 700, 800, 900, 1000 mg/kg or mg/kg, including all values and ranges there between.

$\beta_2$-adrenergic receptor agonist can be administered at a dose of 0.01, 0.1, 0.5, 1, 1.5, 5, 10, 25, 50, 100, 500 mg/kg or mg/kg to 500, 600, 700, 800, 900, 1000 mg/kg or mg/kg, including all values and ranges there between.

A vasodilator is administered at a dose of 0.01, 0.1, 0.5, 1, 1.5, 5, 10, 25, 50, 100, 500 ng/kg or mg/kg or mg/kg to 500, 600, 700, 800, 900, 1000 ng/kg or mg/kg or mg/kg, including all values and ranges there between.

A $\beta_1$-adrenergic receptor antagonist includes, but is not limited to acebutolol, atenolol, betaxolol, bisoprolol, esmolol, metoprolol, or nebivolol. In a particular aspect the $\beta_1$-adrenergic receptor antagonist is esmolol.

In certain aspects the methods, an individual is suffering from chronic stable angina, acute coronary syndrome, cardiac arrest, or is experiencing or recently experienced (e.g. with 1, 5, 10, 20, 30, or 60 minutes of administering a composition of the invention) a myocardial infarction. In particular aspects, the individual has had or is having a myocardial infarction or cardiac arrest. The methods can include the step of administering a composition prior to and/or subsequent to reperfusion or reperfusion therapy. In a certain aspect the step of administering a composition is performed during a myocardial infarction. In a further aspect the step of administering is performed prior to and/or subsequent to resuscitation or resuscitation therapy. In still a further aspect the step of administering is performed during a cardiac arrest.

In certain aspects, the PKA activator and the $\beta_1$-adrenergic receptor antagonist are administered separately or in a single formulation or in separate formulation at or about the same time. In a further aspect the PKA activator and the $\beta_1$-adrenergic receptor antagonist are administered within 0.1, 0.5, 0.6, 0.7, 0.8, 0.9, 1, 2, 3, 4, 5, 6, 7, 8, 9, 10, 20, 30, 40, 50, 60 minutes or hours, including all values and ranges there between, after ischemia, reperfusion, and/or resuscitation.

The compositions of the invention can be administered intravascularly, intraosseusly, intraarterially, transdermally, transmucosally, or by inhalation. In certain aspects the compositions are administered by inhalation. In a particular aspect the compositions are formulated for inhalation or inspiration. The compositions can be contain in an inhaler or inhalation or inspiration devices. In other aspects the compositions can be administered by an intraarterial or intravenous or intracoronary route.

An "effective amount" of a compound can be formulated with a pharmaceutically acceptable carrier to form a pharmaceutical composition before being administered for treatment of a disease. "An effective amount" or "pharmacologically effective amount" refers to the amount of compound that is required to confer therapeutic effect on the treated subject, e.g., reduced reperfusion injury, etc. Effective doses will also vary, as recognized by those skilled in the art, depending on the route of administration, the excipient usage, and the optional co-usage with other therapeutic treatments.

In yet another embodiment of the present invention there is provided a method of reducing drug-induced cardiomyopathy in an individual. Programmed cell death or apoptosis is a phenomenon implicated as one of the key mechanisms underlying the pathogenesis of chemotherapy, i.e., doxorubicin-induced cardiomyopathy. When the cardiotoxic effects of doxorubicin in patients treated for advanced cancer were studied, an incidence of >5% of doxorubicin-induced cardiomyopathy was reported at a dose of 501-550 mg/m$^2$ body surface area, increasing to 30% at over 550 mg/m$^2$ (Lefrak et al., 1973). In animal studies, intravenous calcitonin-gene related peptide (CGRP) infusion or stimulation of myocardial calcitonin-gene related peptide receptors by calcitonin-gene related peptide-receptor agonist, adrenomedullin, exerted a potent anti-apoptotic effect against cardiomyocyte death induced by chemotherapy drug, doxorubicin (Tokudome, 2002) or oxidative stress (Sueur, 2005). This effect suggests that CGRP may exert myocyte protection against doxorubicin-induced myocardial damage during doxorubicin chemotherapy.

In certain aspects a subject may have had, is suspected of having, or is at risk of having an ischemic event. A treated individual can be suffering from chronic stable angina, acute coronary syndrome or is experiencing myocardial infarction.

The composition described herein can be administered prior to, concurrent with, or subsequent to another drug (for instance, a chemotherapeutic agent). In certain aspects, the compositions are administered during reperfusion or reperfusion therapy. The effect of co-administration with the composition is to reduce cardiotoxic effect of the drug without reducing, ameliorating, eliminating, or otherwise interfering with any cytotoxic, cytostatic, apoptotic or other killing or inhibitory therapeutic effect of the drug.

In certain aspects the compositions are formulated for intravenous administration. In a aspect the composition is packaged in container that can be used methods administering the packaged composition in intravenously, for example an I.V. bag or container.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

As used herein, the term "contacting" or "administering" refers to any suitable method of bringing the composition described herein into contact with a intrinsic cardiac adrenergic cell. For in vivo applications, any known method of administration is suitable as described herein.

As used herein, the term "agonist" or "antagonist" means a molecular entity of natural, semi-synthetic, or synthetic origin that either activates or blocks, stops, inhibits, and/or suppresses a target polypeptide or function, e.g., the calcitonin-gene related peptide pathway. For instance, the agonist will activate the pathway while the antagonist will block, stop, inhibit, and/or suppress a pathway.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
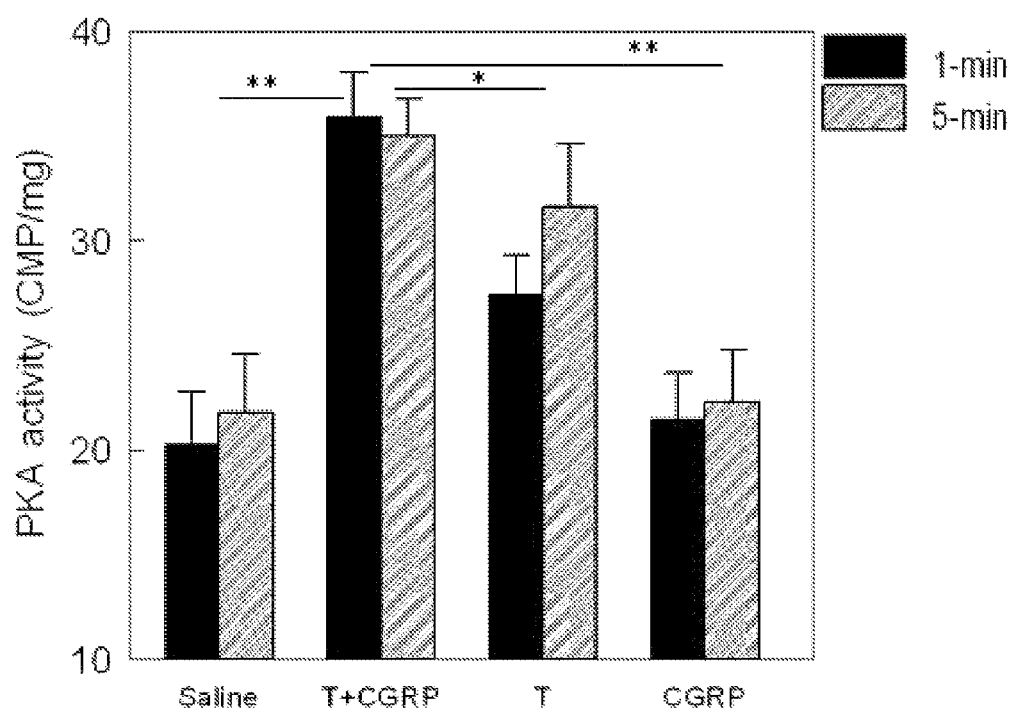
FIG. 1 Synergistic activation of rat ventricular myocardial PKA by the combination therapy with terbutaline and CGRP (T+CGRP) delivered at the time of late-ischemia-early-reperfusion. Saline, terbutaline, CGRP or the combination (T+CGRP) was infused for 10-min via rat tail vein. One or 5 min after infusion, the ventricular tissues were harvested for PKA assay (Huang et al., 2007a). T: terbutaline. **: $p<0.01$, *: $p<0.05$.

The high total direct costs of care of patients experiencing ischemic events presents an urgent need for the development of pharmacological strategies that are safe and effective in the treatment of such disease and condition.

Reperfusion therapy, either percutaneous coronary intervention (PCI) or thrombolysis, is the standard of care of reperfusion for acute myocardial infarction in the United States. PCI has been shown in meta-analyses to decrease mortality compared with thrombolysis. Despite this improvement in outcome, mortality after acute myocardial infarction remains 3-5%. In addition, severe myocardial damage results in heart failure for some heart attack survivors as well as the risk of late sudden death. The inevitable and potentially lethal reperfusion injury poses a continuous (hours to days) myocardial damage process following reperfusion therapy. To date, there is no drug available clinically that has been shown to reduce reperfusion injury following PCI or other modalities of coronary revascularization therapy.

Timely reperfusion salvages myocardium from tissue injury after prolonged ischemia. However, restoration of blood flow to ischemic myocardium may exaggerate injury that is not present at the end of ischemia. This reperfusion injury is primarily expressed as contractile and coronary vascular endothelial dysfunction, upregulation of adhesion molecules on the endothelium, and/or transendothelial migration of inflammatory cells into the parenchyma, edema, infarction, and apoptosis. Embodiments of the present invention provide additional compositions and methods for treating, ameliorating, reducing, and/or limiting this reperfusion injury as well as other cardiac and cardiovascular disorders.

The inventors have described a therapy using methods and combinations with a $\beta_2$-AR agonist (e.g., terbutaline) and a vasodilator (e.g., CGRP) to reduce myocardial infarction size in experimental myocardial ischemia-reperfusion when delivered at the late-ischemia-early-reperfusion phase (International Patent Application No. PCT/US2008/062026 based on U.S. Ser. Nos. 60/926,919 and 60/943,416, each of which is incorporated herein by reference in its entirety). The inventors have further identified that the activation of PKA is the cellular mechanism responsible for the heart protection conferred by the combination therapy of a β2-AR agonist (e.g., terbutaline) and a vasodilator (e.g., CGRP). Thus, the strategy of activating PKA can provide therapy for reducing reperfusion injury during myocardial ischemia-reperfusion in clinical settings.

The inventors have demonstrated that activation of PKA at late-ischemia-early-reperfusion phase confers infarct-size limiting effect. In certain aspects of the invention, administration of a PKA activator (e.g., a phosphodiesterase inhibitor milrinone) reduces infarct size robustly. Furthermore, administration of a combination a PKA activator (e.g., milrinone) and a $\beta_1$-AR antagonist (e.g., esmolol) confers synergistic infarct-size reducing or limiting effect in a MI model.

The inventors have further demonstrated that the observed infarct-size limiting or reducing effect by administrating a PKA activator and a $\beta_1$-AR antagonist is a result of PKA activation. When delivered 30-min after the onset of ischemia, the administration of a combination a PKA activator and a $\beta_1$-AR antagonist to ventricular myocytes reduces myocyte death rate significantly, whereas blockade of PKA abolishes the myocyte protection induced by the combination therapy.

I. CGRP

The intrinsic cardiac adrenergic (ICA) cell synthesizes and releases epinephrine, an endogenous $\beta_2$-adrenoreceptor ($\beta_2$-AR) agonist that exerts potent myocardial infarct-size-limiting effect via $\beta_2$-AR stimulation in a rat model (Huang et al., 2007b). The inventors have described methods and compositions using ICA cell-derived epinephrine for heart disease treatment. Recently, the inventors have discovered that the ICA cell synthesizes and releases a neuropeptide, namely calcitonin gene-related peptide (CGRP), in human and rat hearts. The prepro-form of human CGRP has an amino acid sequence of RIIAQKRACDTATC VTHRLAGLLSRSGGV-VKNNFVPTNVGSKAFGRRRRDLQA (SEQ ID NO:1). Aspects of the invention include peptides of at least, at most, or about 5, 6, 7, 8, 9, 10, 11, 12, 13, 14, 15, 16, 17, 18, 19, 20, 21, 22, 23, 24, 25, 2, 27, 28, 29, 30, 31, 32, 33, 34, 35, 36, 37, 38, 39, 40, 41, 42, 43, 44, 45, 46, 47, 48, 49, 50, 51, 52, and 53 contiguous amino acids of SEQ ID NO:1 or mimetics or variants thereof. The broad implications of intrinsic cardiac adrenergic cells have been linked to developmental biology, cardiac impulse generation and conduction, blood pressure regulation, post-transplanted heart function and heart protection against myocardial infarction (Huang et al., 2007b).

The magnitude of infarct-size-limiting effect provided by combination therapy of a PKA activator and a $\beta_1$-AR antagonist is impressive even delivered in a delayed fashion (i.e., 30-min after the onset coronary artery occlusion). This phenomenon has particular clinical relevance, since most patients with acute heart attack have already experience coronary artery occlusion for 30-min to 1-hr or longer before arriving at a hospital. The cardioprotective effect demonstrated here can revolutionize the concept and management of MI treatment. In certain embodiments, kits for emergency administration can be provided. The therapy described herein can be administered on site by emergency personnel or others present when the subject experiences such an episode. In other aspects, the compositions and methods can prevent or rescue heart muscle damage in patients suffering from acute MI.

II. Reperfusion Injury

Ischemia is a deficiency of blood or blood flow in a tissue typically due to functional constriction or actual obstruction of a blood vessel. Such a deficiency result in an infarct, an area of cell death in a tissue due to local ischemia resulting from obstruction of circulation to the area, most commonly by a thrombus, embolus, ruptured or obstructing atherosclerotic plaque. When the constriction or obstruction is removed and blood flow restored reperfusion occurs. Although blood flow is restored, the reperfusion can also result in adverse effects including cellular swelling and necrosis, apoptosis, edema, hemorrhage, no-reflow phenomenon, and tissue damage by free oxygen radicals.

Reperfusion injury to the heart is accompanied by the upregulation and post-translational modification of a number of proteins normally involved in regulating cell cycle progression. Disclosed are methods and compositions for reducing reperfusion injury including, but not limited to reduction or limitation of infarct size. In certain aspects, the methods are equally appropriate for use in reducing injury following stroke including, but not limited to ischemic strokes (including strokes resulting from cerebral thrombosis, cerebral embolism, and atrial fibrillation), hemorrhagic strokes (including strokes resulting from aneurysm and arteriovenous malformation), and transient ischemic attack, reducing infarct size following pulmonary infarction, reducing renal ischemia injury, reducing ischemic/reperfusion injury occurring during cardiac surgery where a heart lung machine is used such as coronary artery bypassing, and reducing reperfusion injury occurring during the preservation of organs for transplant.

Generation of abundant oxygen free radicals during early reperfusion has been implicated as a major player in the pathogenesis of tissue injury associated with reperfusion. The burst of oxygen-derived free radicals occurs within the first minute and peaks at 4 to 7 min after reperfusion; increased free radical generation is still detectable during later periods of reperfusion. Superoxide anions have been implicated in lipid peroxidation of biological membranes, triggering adhesion molecule expression on endothelium, and subsequent initiation of neutrophil and endothelial cell interactions. Both in vivo and in vitro studies have shown that oxygen free radicals are potent stimuli for the rapid upregulation of P-selectin and ICAM-1 on endothelium as well as initiation of acute inflammation and subsequent recruitment of neutrophils in ischemic myocardium.

A condition that is similar to MI and can be treated using compositions and methods described herein is resuscitation injury. Cardiorespiratory arrest is the abrupt cessation of normal circulation of the blood due to failure of the heart to contract effectively during systole, which is also an ischemic process. Although a cardiorespiratory arrest is a different type from myocardial infarction, cardiac resuscitation to reestablish circulation is equivalent to reperfusion.

III. Methods and Compositions for Reducing Ischemic Injury

"Treatment" and "treating" refers to the medical management of a subject with the intent to cure, ameliorate, stabilize, or prevent a disease, condition, or disorder. This term includes active treatment, i.e., treatment directed specifically toward the improvement of a disease, condition, or disorder. Treatment and treating also include causal treatment, i.e., treatment directed toward removal of the cause of the associated disease, condition, or disorder. In addition, this term includes palliative treatment, i.e., treatment designed for the relief of symptoms rather than the curing of the disease, condition, or disorder; preventative treatment, i.e., treatment directed to minimizing or partially or completely inhibiting the development of the associated disease, condition, or disorder; and supportive treatment, i.e., treatment employed to supplement another specific therapy directed toward the improvement of the associated disease, condition, or disorder. It is understood that treatment, while intended to cure, ameliorate, stabilize, or prevent a disease, condition, or disorder, need not actually result in the cure, ameliorization, stabilization, or prevention. It is understood and herein contemplated that "treatment" does not necessarily refer to a cure of the disease or condition nor a complete prevention of infarct, but can involve, for example, an improvement in the outlook of an reperfusion injury. The effects of treatment can be measured or assessed as described herein and as known in the art as is suitable for the disease, condition, or disorder involved (e.g., MI, etc.). Such measurements and assessments can be made in qualitative and/or quantitative terms. Thus, for example, characteristics or features of a disease, condition, or disorder and/or symptoms of a disease, condition, or disorder can be reduced to any effect or to any amount. Also, for example, treating reperfusion injury can comprise any method or the administration of any combination of a PKA activator and a $\beta_1$-AR antagonist that affects tissue damage resulting from reperfusion or ameliorates the degree of or potential for tissue injury associated with an ischemia/reperfusion event.

"Reducing," "reduce," or "reduction" in the context of a disease or condition herein refers to a decrease in the cause, symptoms, or effects of a disease or condition. Therefore, in the disclosed methods, "reducing" can refer to a 10%, 20%, 30%, 40%, 50%, 60%, 70%, 80%, 90%, or 100% decrease, or any value or range there between, in the amount of injury or area of injury due to reperfusion or resuscitation, including but not limited to infarct size, cardiac function, etc.

Disclosed are compositions and methods of reducing reperfusion injury in a subject in need thereof comprising administering to the subject a composition comprising a PKA activator and/or a $\beta_1$-AR antagonist. One manifestation of reducing reperfusion injury is reducing or limiting or ameliorating infarct size. Disclosed herein are methods of reducing infarct size following a reperfusion or resuscitation event in a subject comprising administering to the subject the inventive compositions and/or methods that inhibit, reduce, limit, or ameliorate an infarct.

It is understood that there are many known causes of reperfusion injury. For example, a reperfusion injury can result from ischemia/reperfusion event such as myocardial ischemia, myocardial reperfusion, subendocardial ischemia, Takayasu's arteritis, including but not limited to (ischemic strokes (including strokes resulting from cerebral thrombosis, cerebral embolism, and atrial fibrillation), hemorrhagic strokes (including strokes resulting from aneurysm and arteriovenous malformation), and transient ischemic attack), pulmonary infarction, hypoxia, retinal ischemia, renal ischemia, cardiac surgery where a heart lung machine is used such as coronary artery bypassing, and preservation of organs for transplant. Thus, also disclosed herein are methods of reducing reperfusion injury comprising administering a composition comprising a PKA activator and/or a $\beta_1$-AR antagonist, wherein the reperfusion injury occurs following an ischemia/reperfusion/resuscitation event that includes, but is not limited to myocardial ischemia, myocardial reperfusion, subendocardial ischemia, Takayasu's arteritis, stroke, ischemia strokes, cerebral thrombosis, cerebral embolism, atrial fibrillation, hemorrhagic strokes, aneurysm and arteriovenous malformation, transient ischemia attack, pulmonary infarction, hypoxia, retinal ischemia, renal ischemia, cardiorespiratory arrest, ischemic/reperfusion event occurring during cardiac surgery where a heart lung machine is used such as coronary artery bypassing, and/or ischemic/reperfusion events occurring during the preservation of organs for transplant.

It is contemplated that the disclosed methods and compositions can be used to reduce reperfusion injury following an ischemic event. Thus, for example, disclosed are methods of reducing reperfusion injury in a subject in need thereof comprising administering to the subject a composition comprising a PKA activator and/or a $\beta_1$-AR antagonist, wherein the agents are administered at least, at most or about 0.1, 0.5, 1, 1.5, 2, 2.5, 5, 6, 7, 8, 9, 10, 11, 12, 13, 14, 15, 16, 17, 18, 19, 20, 21, 22, 23, or 24 minutes or hours, including all values and ranges there between, before or following a reperfusion or reperfusion therapy or resuscitation event. It is understood that the more quickly the composition can be administered following the reperfusion event, the less the likelihood of injury and subsequently the greater the potential reduction in infarct size and benefit to the subject. Thus, disclosed herein are methods wherein the agent is administered within 24, 12, 6, 2, 1 hour(s) to 30, 15, 10, 5 minutes (typically after the onset of or after ischemia) before or during or following reperfusion or reperfusion therapy or resuscitation. It is understood that administration of the agent can occur at any time between 5 minutes and 24 hours before or during or following the ischemia/reperfusion/resuscitation event. It is also understood that ischemia and reperfusion are not only physiologically different events, but do not necessarily occur at the same time. As ischemia refers to deficiency of blood to a tissue or cell typically due to a thrombus or embolus and reperfusion injury results when the obstruction or constriction is removed, it is possible and desirable to reduce reperfusion injury during or after the ischemia/reperfusion event. Thus, for example, a composition comprising a PKA activator and a $\beta_1$-AR antagonist could be administered during the ischemia or alternatively after the ischemia, but before reperfusion has occurred, or alternatively after the ischemia and at the time of or during or after reperfusion. Thus, disclosed herein are methods wherein the agents are administered during the ischemia and/or reperfusion event.

In certain embodiments the composition comprising a PKA activator and a $\beta_1$-AR antagonist is administered before the ischemia and/or reperfusion and/or resuscitation event. Thus, it is contemplated that individuals at risk for or having a history of ischemia/reperfusion events can decrease the risk of further necrosis in future events by administration of a PKA activator and a $\beta_1$-AR antagonist composition prophylactically, which also includes prior to, during, or after catheterization or other medical or surgical procedures such as coronary artery bypass surgery. It is also understood that many ischemia/reperfusion events have early warning symptoms preceding the actual event which when recognized can allow the subject to seek immediate treatment. Even if there is ischemic/reperfusion injury caused by future ischemia/reperfusion events, it is contemplated that the prophylactic administration of a PKA activator and a $\beta_1$-AR antagonist composition will reduce infarct size. For example, disclosed herein are methods of reducing ischemia/reperfusion injury in a subject in need thereof (having, had, or at risk of having an ischemic/reperfusion event) comprising administering to the subject a PKA activator and a $\beta_1$-AR antagonist composition that, wherein the composition is administered at least 30 minutes before the ischemia/reperfusion event. Thus, disclosed herein are methods wherein the agent is administered 15, 30 minutes, 1, 2, 6, 12, 24 hour(s), 2, 3 days, 1, or 2 weeks or any time point in between before the ischemia/reperfusion event.

In particular aspects, compositions of the invention can be administered before, during, and/or after percutaneous transluminal coronary angioplasty, vascular grafts in surgical revascularization (before removal of the aortic cross-clamp in on-pump cardiac surgery), removal of the target vessel ligature during off-pump coronary artery bypass graft surgery, organ transplantation, resuscitation measures or activities, or other procedures of events that impede or will impede or have impeded blood flow to myocardium or other organs or tissues.

The present invention is directed to a method of treating an individual at risk or with established cardiovascular disorder, comprising the steps of: administering to the individual a pharmacologically effective amount of a composition that activates PKA in intrinsic cardiac adrenergic cells within heart of the individual. In general, the activation of PKA may reduce myocardial infarct size, may improve cardiac hemodynamic performance, may improve heart failure symptoms, may reduce apoptotic effect of a cardiotoxic drug or combinations thereof. The composition that is administered in this method may comprise a PKA activator and/or a $\beta_1$-AR antagonist. Representative examples of a useful a PKA activator may include but is not limited to a phosphodiesterase inhibitor, or a $\beta_2$-adrenergic receptor agonist, or a composition comprising a vasodilator and/or a $\beta_2$-adrenergic receptor agonist. A phosphodiesterase inhibitor includes, but is not limited to milrinone, enoximone, vinpocetine, erythro-9-(2-hydroxy-3-nonyl)adenine, mesembrine, rolipram, ibudilast, sildenafil, tadalafil, vardenafil, udenafil, or avanafil. A $\beta_2$-adrenergic receptor agonist includes but is not limited to epinephrine, metaproterenol, terbutaline, albuterol, biterol, dobutamine, dopamine, epinephrine, formoterol, isoproterenol, levalbuterol, metaproterenol, salmeterol, or ritodrine. Furthermore, a vasodilator includes but is not limited to CGRP, adrenomedullin, or amylin. Additionally, the cardiovascular disorder that the individual has or is at risk of developing may include, but is not limited to myocardial ischemia, myocardial dysfunction, drug-induced cardiomyopathy or hypertension. Furthermore, the drug in the drug-induced cardiomyopathy may include but is not limited to a chemotherapeutic agent. Examples of the chemotherapeutic agent may include but is not limited to doxorubicin (Adriamycin) or daunorubicin (Cerubidine).

The present invention is further directed to a method of reducing drug-induced cardiomyopathy in an individual, comprising: administering to the individual a pharmacological effective amount of a composition that activates PKA in intrinsic cardiac adrenergic cells within heart of the individual, where the activation of PKA reduces apoptotic effect of the drug, thereby reducing the drug-induced cardiomyopathy in the individual. In general, the activation of PKA may reduce myocardial infarct size, may improve cardiac hemodynamic performance, may improve heart failure symptoms, may reduce apoptotic effect of a cardiotoxic drug or combinations thereof. The composition that is administered in this method may comprise a PKA activator and/or a $\beta_1$-AR antagonist. Representative examples of a useful a PKA activator includes, but is not limited to phosphodiesterase inhibitor, or $\beta_2$-adrenergic receptor agonist, or a composition comprising vasodilator and $\beta_2$-adrenergic receptor agonist. A phosphodiesterase inhibitor includes, but is not limited to milrinone, enoximone, vinpocetine, erythro-9-(2-hydroxy-3-nonyl)adenine, mesembrine, rolipram, ibudilast, sildenafil, tadalafil, vardenafil, udenafil, or avanafil. A $\beta_2$-adrenergic receptor agonist includes but is not limited to epinephrine, metaproterenol, terbutaline, albuterol, biterol, dobutamine, dopamine, epinephrine, formoterol, isoproterenol, levalbuterol, metaproterenol, salmeterol, or ritodrine. Furthermore, a vasodilator includes, but is not limited to CGRP, adrenomedullin, or amylin. The composition in such a method may be administered prior to, concurrent with, or subsequent to the administration of the drug. Examples of the drug may include but is not limited to a chemotherapeutic agent. Additionally, examples of the chemotherapeutic agent may include but is not limited to doxorubicin (Adriamycin) or daunorubicin (Cerubidine).

A. Activation and Inhibition of Protein Kinase A

Protein kinase A (PKA), also known as cAMP-dependent protein kinase, is a family of enzymes whose activity is dependent on the level of cyclic AMP (cAMP) in the cell. PKA can catalyze the transfer a phosphate group from ATP to protein substrates. This phosphorylation usually results in a change in activity of the substrate protein. PKAs are present in a variety of cells and act on different substrates. PKAs in myocytes are involved in regulation of glucose production.

The holoenzyme of PKA comprises two types of subunits: regulatory and catalytic subunits. When the level of cAMP is low, the holoenzyme of PKA remains intact and is catalytically inactive. When the concentration of cAMP rises, cAMP binds to the regulatory subunits and leads to an allosteric change in PKA conformation which releases the catalytic subunits and activates PKA. Inhibition of protein kinase A occurs when cAMP level is reduced by a phosphodiesterase, which quickly converts cAMP to AMP.

The phosphodiesterases (PDE) comprise a group of enzymes that degrade the phosphodiester bond in the second messenger molecules cAMP and cGMP Inhibitors of PDE can prolong or enhance the effects of physiological processes mediated by cAMP or cGMP by inhibition of their degradation by PDE.

Milrinone is a PDE III inhibitor. Milrinone: can be used clinically for short-term treatment of cardiac failure. It mimics sympathetic stimulation and increase cardiac output. Phosphodiesterase inhibitors such as milrinone are not indicated for the treatment of acute myocardial infarction. Milrinone is only indicated for temporarily treatment of decompensated congestive heart failure symptoms. It may temporarily improve hemodynamic state and relieve the symptoms. However, milrinone exerts no heart protection. On the contrary, long-term use of milrinone increases mortality in patients with congestive heart failure (Packer 1991). Recent clinical trials demonstrated that intravenous milrinone therapy causes more harm in heart failure patients with etiology of ischemic cardiomyopathy (i.e., heart failure caused by myocardial infarction). Milrinone-treated patients with ischemic etiology have worse outcomes than those treated with placebo in terms of the composite of death or rehospitalization (Felker 2003).

In a rat model, administration of milrinone before the onset of acute myocardial infarction confers subsequent infarct-size reduction (Sanada 2001), a heart protective phenomenon termed ischemia preconditioning. However, it is unclear whether milrinone confers heart protection when it is given after the onset of acute myocardial infarction. As a matter of fact, in a canine model, administration of milrinone 30-min after the onset of acute myocardial infarction showed no infarct-size reduction (Campbell 1987). Thus, neither clinical trials nor experimental studies have demonstrated cardiac benefit of milrinone given to the patients who have had acute myocardial infarction or congestive heart failure due to ischemic cardiomyopathy.

It is important to distinguish two complete different states of drug delivery time (i.e., before, during, or after the onset of acute myocardial infarction). An experimental condition that a drug is given before the onset of induced acute myocardial infarction does not occur in clinical reality. It represents only a laboratory curiosity. One cannot predict when an unannounced heart attack will happen and accordingly, administer a drug to the patient just before such an event to protect the heart. Thus, the preconditioning phenomenon has little real-world clinical value. In contrast, administration of a drug after the onset of heart attack is a real clinical situation when patients with chest pain arrive in hospital seeking for the treatment. A drug that can be given after the onset of heart attack confers heart protection and has true clinical value. Thus, the discovery of heart protective effect conferred by a drug administered before the onset of heart attack (i.e., preconditioning) is not equivalent to the discovery of heart protective effect induced by the same drug that is administered after the onset of the heart attack.

For example, erythropoietin which showed infarct-size reduction when given before the onset of ischemia in animal model (Cai 2003) conferred no improvement on heart function when it was administered to the patients after acute myocardial infarction (Lipsic 2006). Clearly, until proven otherwise, the pharmacological ischemia preconditioning cannot predict or generalize the same outcome when the same agent is administered in post-infarction state (postconditioning). The findings from the preconditioning and postconditioning are independent discoveries. They are different concepts with different value.

In certain aspects PDE III inhibitors include, but are not limited to milrinone, cilostamide, enoximone, olprinone, toborinone, and levosimendan. In another aspect, PDE IV inhibitor include, but are not limited to rolipram and piclamilast.

B. β1-Adrenergic Receptor (β1-AR) Antagonist

β1-adrenergic receptor (β-AR) antagonists (or β-blockers) are a class of drugs used for various indications, but particularly for the management of cardiac arrhythmias and cardioprotection after myocardial infarction. Esmolol is one of the β-adrenergic receptor antagonists. It has been used for the treatment of cardiac arrhythmia. Although β-blockers have been used routinely in the treatment of acute myocardial infarction with clear benefit, it has been controversial with respect to whether β-blocker actually reduces infarct-size. While some clinical studies demonstrated infarct-size reduction by β-blockers (Anonymous 1986, Roque 1987), other trials failed to support such an effect (Rude 1986, Heber 1987, Van de Werf 1993, Ellis 2001). Similarly, inconsistent results regarding (3-blocker-mediated infarct-size-reduction have been reported in animal models (Kudoh 1984).

C. β2-Adrenergic Receptor (β2-AR) Agonist

β2-AR agonists act on the β2-adrenergic receptor causing smooth muscle relaxation resulting in dilation of bronchial passages, vasodilation in muscle and liver, relaxation of uterine muscle and release of insulin. All clinically approved β2 agonists are available in inhaler form (either metered-dose inhalers, which aerosolize the drug, or dry powder which can be breathed in).

Salbutamol (known as albuterol in the U.S.) also comes in a liquid form for nebulization, which is more commonly used in emergency rooms than inhalers. Salbutamol and terbutaline are also both available in oral forms.

In addition, several of these medications are available in intravenous forms including both salbutamol and terbutaline. It can be used in this form in severe cases of asthma, but more commonly it is used to suppress premature labor because it also relaxes uterine muscle, thereby inhibiting contractions.

β2-AR agonists can typically be divided into two groups: (1) short-acting and (2) long-acting. Short-acting β2 agonists include, but are not limited to, salbutamol (albuterol), levalbuterol, terbutaline, pirbuterol, procaterol, metaproterenol, fenoterol, or bitolterol mesylate. Long-acting β2 agonists include, but are not limited to, salmeterol, formoterol, or bambuterol.

D. Vasodilators

Vasodilation is a process where blood vessels in the body develop a wider internal diameter (dilate) following the relaxation of the smooth muscle in the vessel wall. This effect will reduce systemic arterial pressure (blood pressure). Vasodilation also occurs in superficial blood vessels of warm-blooded animals when the ambient environmental temperature increases as a method of heat dissipation, i.e., this process diverts the flow of heated blood to the skin of the animal, where heat can be more easily released into the atmosphere. The opposite physiological process is called vasoconstriction.

A vasodilator is a substance that causes vasodilation. Several vasodilators are used as drugs which may, for example, allow blood to flow more easily around a clot. Vasodilators include, but are not limited to CGRP, adrenomedullin, amylin, adenosine (e.g., adenocard and alpha blockers), amyl nitrite and other nitrites, L-Arginine, atrial natriuretic peptide (ANP), bradykinin, ethanol, endothelium-derived hyperpolarizing factor (EDHF), histamine, niacin (nicotinic acid), nitric oxide, glyceryl trinitrate, isosorbide mononitrate, isosorbide dinitrate, pentaerythritol tetranitrate (PETN), sodium nitroprusside, PDE5 inhibitors (sildenafil, tadalafil, vardenafil), platelet activating factor (PAF), prostacyclin (PGI2) and other prostaglandins, tetrahydrocannabinol (THC), theobromine, and papaverine.

Calcium Gene-Related Peptide CGRP is a neuropeptide distributed in the central and peripheral sensory nervous systems. CGRP is a potent vasodilator that has important implication in blood pressure regulation (Brain, 2004). The cardiac effects of CGRP include an inotropic effect on isolated human (Saetrum et al., 2000) and animal ventricular muscle (Miyauchi et al., 1988; Van Gelderen et al., 1995) and isolated rat ventricular myocytes (Huang et al., 1999). Several clinical trials have demonstrated the benefit of CGRP in improving cardiac output in chronic heart failure (CHF) patients (Anand et al., 1991, Dobois-Rande et al., 1992, Gennari et al., 1990, Shekhar et al., 1991). Intravenous CGRP infusion improves heart function in advanced CHF patients (Gennari et al., 1990). In dilated cardiomyopathic patients CGRP infusion exerts dose-dependent increase in cardiac output associated with reduced pulmonary arterial wedge pressure (Anand et al., 1991).

CGRP is a potent vasodilator of human coronary arteries (Gulbenkian, 1993; Hasbak 2003). Intravenous CGRP infusion significantly dilates small coronary arteries at normal and atheromatous sites (Uren et al., 1993; Lundman et al., 1991) delaying the onset of myocardial ischemia during exercise in patients with stable angina (Uren et al., 1993). CGRP also mediates myocardial ischemic preconditioning via its infarct-size-limiting effect (Lu et al., 2001; Wolfrum et al., 2005).

In the human heart, CGRP-expressing nerve endings derived from paravertebral dorsal root ganglia are only scarcely distributed to epicardial coronary arteries. They are absent in the deeper layers of ventricular myocardium (Chow et al., 1993). It is unclear whether any type of heart cell produces CGRP thereby exerting direct cardiac modulation. The inventors have discovered that ICA cells synthesize and release CGRP. The inventors also contemplate that CGRP and epinephrine co-released from ICA cells confer synergistic protection against myocardial ischemia. Furthermore, the inventors contemplate that synergistic cardioprotection mediated by endogenous CGRP and epinephrine can be simulated by combination therapy with exogenous CGRP and $\beta_2$-AR agonist.

Calcitonin-gene related peptide exerts significant myocardial protection against ischemia via two mechanisms. First, calcitonin-gene related peptide is a potent systemic and coronary arterial vasodilator (Brain and Grant, 2004). Calcitonin-gene related peptide induces concentration-dependent relaxation of isolated human coronary arteries (Gulbenkian et al., 1993). Intravenous infusion of calcitonin-gene related peptide significantly dilates small coronary arteries at normal and atheromatous stenotic sites (Uren et al., 1993). It also delays onset of myocardial ischemia during treadmill exercise testing in patients with chronic stable angina (Uren et al., 1993). Secondly, calcitonin-gene related peptide mediates myocardial ischemic preconditioning (Luo et al., 2004; Wolfrum et al., 2005). Endogenous calcitonin-gene related peptide has infarct-size limiting effect during myocardial infarction, an effect mimicking ischemia preconditioning.

IV. Pharmaceutical Formulations and Delivery

Methods of the present invention include the delivery of an effective amount of a PKA activator and/or a $\beta_1$-AR antagonist. An "effective amount" or "pharmacologically effective amount" of a pharmaceutical composition, generally, is defined as that amount sufficient to detectably and repeatedly achieve the stated desired result, for example, to ameliorate, reduce, minimize or limit the extent of the disease or its symptoms (e.g., reperfusion injury). Other more rigorous definitions may apply, including elimination, eradication or cure of disease or condition. The interrelationship of dosages for animals and humans (based on milligrams per square meter of body surface) is described by Freireich et al. (1966). Body surface area may be approximately determined from height and weight of the patient. See, e.g., Scientific Tables (1970).

A. Administration

In certain embodiments, it is desired to limit, reduce, or ameliorate infarct size and/or reverse or reduce reperfusion injury. The routes of administration will vary, naturally, with the location and nature of the lesion or site to be targeted, and include, e.g., regional, parenteral, pulmonary, intravenous, intramuscular, and/or systemic administration and formulation. Direct injection or injection into the vasculature or the vessels to and from and within an organ or tissue is specifically contemplated for target areas. Local, regional, or systemic administration also may be appropriate.

Multiple injections delivered as a single dose comprise at least, at most or about 0.01 to 0.5 ml volumes or more, including all values and ranges there between. Compositions of the invention may be administered in multiple injections to a targeted site.

Continuous administration over a period of time also may be applied where appropriate, for example, where a catheter or intravenous (IV) system is used to administer the present treatment or as an adjunct to another standard treatment for ischemia and it associated complications. Delivery via syringe or catherization is specifically contemplated. Such continuous perfusion may take place for a period from about 0.5-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

Treatment regimens may vary as well and often depend on target site, subject condition, and health and age of the patient. Certain conditions will require more aggressive treatment. The clinician will be best suited to make such decisions based on the known efficacy and toxicity (if any) of the therapeutic formulations or methods.

Treatments may include various "unit doses." A unit dose is defined as containing a predetermined quantity of a therapeutic composition(s). The quantity to be administered, and the particular route and formulation, are within the skill of those in the clinical arts. A unit dose need not be administered as a single injection but may comprise continuous infusion over a set period of time. A unit dose may conveniently be described in terms of μg, ng, or mg of component. Alternatively, the amount specified may be the amount administered per subject weight (typically kg) or as the average daily, average weekly, or average monthly dose.

Components can be administered to a subject in a dose or doses of about or of at least about 0.5, 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 μg, ng, mg or mg, or more, or any range derivable therein. Alternatively, the amount specified may be the amount administered as the average daily, average weekly, or average monthly dose, or it may be expressed in terms of ng/kg, mg/kg, or mg/kg, where kg refers to the weight of the subject or patient. In other embodiments, the amount specified is any number discussed above but expressed as mg/m$^2$ (with respect to target, organ, or tissue surface area).

Toxicity and therapeutic efficacy of active ingredients can be determined by standard pharmaceutical procedures, e.g., for determining LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

B. Injectable Compositions and Formulations

In some embodiments, the method for the delivery of a PKA activator and a $\beta_1$-AR antagonist composition is via intraarterial or intravenous administration. Injection of a PKA activator and a $\beta_1$-AR antagonist composition may be delivered by syringe or catheter or any other method used for injection of a solution, as long as the PKA activator and the $\beta_1$-AR antagonist composition and any associated components can pass through the particular gauge of needle or device required for injection or intravascular delivery.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, mixtures thereof, and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In certain formulations, a water-based formulation is employed while in others, it may be lipid- or oil-based. In particular embodiments of the invention, a composition comprising one or more of the components of the described methods and compositions is in a water-based formulation. In other embodiments, the formulation is lipid based.

For aqueous solutions, the solution should be suitably buffered if necessary. A liquid diluent is typically rendered isotonic with sufficient saline or glucose. These aqueous solutions are especially suitable for intravenous administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

As used herein, a "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human.

The compositions are administered in a manner compatible with the dosage formulation, and in such amount as will be therapeutically effective. The quantity to be administered depends on the subject to be treated, including, e.g., the length and severity of an ischemic event. Precise amounts of active ingredient required to be administered depend on the judgment of the practitioner. Suitable regimes for initial administration and subsequent administration are also variable, but are typified by an initial administration followed by other administrations. Such administration may be systemic, as a single dose, continuous over a period of time spanning 10, 20, 30, 40, 50, 60 minutes, and/or 1, 2, 3, 4, 5, 6, 7, 8, 9, 10, 11, 12, 13, 14, 15, 16, 17, 18, 19, 20, 21, 22, 23, 24 or more hours, and/or 1, 2, 3, 4, 5, 6, 7, days or more.

C. Combination Treatments

In certain embodiments, the compositions and methods of the present invention involve PKA activator and $\beta_1$-AR antagonist components. These compositions can be used in combination with a second therapy to enhance the effect of the therapy, or increase the therapeutic effect of another therapy being employed. These compositions would be provided in a combination effective to achieve the desired effect, such as the reperfusion of an ischemic area and/or the inhibition of ischemia/reperfusion injury. This process may involve contacting the target area with a composition of the invention and/or a second therapy at the same or different time. This may be achieved by contacting the target area with one or more devices, compositions or pharmacological formulation that includes one or more of the agents, or by contacting the target area or region with two or more distinct devices, compositions or formulations, wherein one composition provides (1) a PKA activator and a $\beta_1$-AR antagonist (e.g., esmolol); and/or (2) a second therapy. A second composition or method may be administered that includes mechanical manipulation, a chemotherapy, radiotherapy, surgical therapy, immunotherapy or gene therapy.

It is contemplated that one may provide a patient with the PKA activator and $\beta_1$-AR antagonist composition therapy and the second therapy simultaneously or within about 0.5 to 12 to 24 minutes or hours of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 minutes, hours, days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the agent(s). Moreover, after a course of treatment, it is contemplated that there is a period of time at which no treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed, for example PKA activator (e.g., a phosphodiesterase inhibitor milrinone) and $\beta_1$-AR antagonist (e.g., esmolol) composition therapy is "A" and a second therapy is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A B/A/B/B B/A/A/B A/A/A/B B/A/A/A A/B/A/A A/A/B/A

Administration of any compound or therapy of the present invention to a patient will follow general protocols for the administration of such compounds or therapy, taking into account the toxicity or potential complications, if any, of the other agent or therapy. Therefore, in some embodiments there is a step of monitoring toxicity or complications that are attributable to combination therapy. It is expected that the treatment cycles would be repeated as necessary. It also is contemplated that various standard therapies, as well as surgical intervention, may be applied in combination with the described therapy.

Disclosed are the components to be used to prepare the disclosed compositions to be used within the methods disclosed herein. These and other materials are disclosed herein, and it is understood that when combinations, subsets, groups, etc. of these materials are disclosed that specific reference to an individual and collective combination and permutation of these compounds may not be explicitly disclosed, each is specifically contemplated and described herein. For example, if a particular PKA activator (e.g., a phosphodiesterase inhibitor milrinone) and $\beta_1$-AR antagonist (e.g., esmolol) is disclosed and discussed and a number of modifications that can be made to a number of molecules are discussed, specifically contemplated is each and every combination and permutation of PKA activator (e.g., a phosphodiesterase inhibitor milrinone) and $\beta_1$-AR antagonist (e.g., esmolol) and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

V. Variants of PKA Activator and $\beta_1$-AR Antagonist

It is also understood that one way to define any known variants and derivatives or those that might arise, of the disclosed compounds and/or peptides herein is through defining the variants and derivatives in terms of homology or identity to specific known sequences or compounds. For example SEQ ID NO. 1 sets forth a particular sequence of a CGRP. Specifically disclosed are variants of these and other peptides herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the stated sequence. Those of skill in the art readily understand how to determine the homology of two proteins or nucleic acids. For example, the identity can be calculated after aligning the two sequences.

Protein or peptide variants and derivatives are well understood to those of skill in the art and can involve amino acid sequence modifications or mimetics. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein or peptide sequence. Typically, no more than about from 2 to 6 residues are deleted at any one site within the molecule. These variants ordinarily are prepared by site specific mutagenesis of nucleotides in the DNA encoding the protein, thereby producing DNA encoding the variant, and thereafter expressing the DNA in recombinant cell culture. Amino acid substitutions are typically of single residues, but can occur at a number of different locations at once; insertions usually will be on the order of about from 1 to 10 amino acid residues; and deletions will range about from 1 to 30 residues.

Substitutional variants are those in which at least one residue has been removed and a different residue inserted in its place. Substantial changes in function or immunological identity are made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one having a substantially smaller side chain, e.g., glycine, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides or peptide provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g., Arg, is accomplished for example by deleting one of the basic residues or substituting one by glutaminyl or histidyl residues.

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH— (cis and trans), —$COCH_2$—, —CH(OH) $CH_2$—, and —$CHH_2SO$— (These and others can be found in Spatola (1983a); Spatola (1983b); Morley (1980); Hudson et al., (1979) (—$CH_2NH$—, $CH_2CH_2$—); Spatola et al. (1986) (—$CHH_2$—S); Hann (1982) (—CH—CH—, cis and trans); Almquist et al. (1980) (—$COCH_2$—); Jennings-White et al. (1982) (—$COCH_2$—); EP 45665 CA (1982) (—CH(OH) $CH_2$—); Holladay et al. (1983) (—C(OH)$CH_2$—); and Hruby (1982) (—$CH_2$—S—); each of which is incorporated herein by reference. A particular non-peptide linkage is —$CH_2NH$—. It is understood that peptide analogs can have more than one atom between the bond atoms, such as β-alanine, γ-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch, 1992), incorporated herein by reference).

It is understood that the compositions disclosed herein have certain functions, such as a PKA activator (e.g., a phosphodiesterase inhibitor milrinone) and a $β_1$-AR antagonist (e.g., esmolol). Disclosed herein are certain structural requirements for performing the disclosed functions, and it is understood that there are a variety of structures which can perform the same function which are related to the disclosed structures, and that these structures will ultimately achieve the same result, for example activation of PKA or inhibition of $β_1$-AR receptor.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

VI. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Exogenous CGRP-β2-AR Agonist Confers Synergistic Cardioprotection and PKA Activation Background: $β_2$-adrenoreceptor ($β_2$-AR) agonist has have been used clinically for asthma treatment for 20 years with favorable clinical safety profile. While calcitonin gene-related peptide (CGRP) is still an investigational drug, it has been tested in numerous clinical trials. CGRP has a favorable clinical safety profile based on the literature. Thus, the combination therapy with $β_2$-AR agonist and CGRP may provide a readily available approach which can quickly translate basic science knowledge into clinical practice. $β_2$-AR stimulation and CGRP secretion each confers infarct-size (IS) reduction during experimental myocardial infarction (MI). The inventors have hypothesized that (1) endogenous stimulation of CGRP-receptor and $β_2$-AR exerts synergistic IS-reduction and (2) that IS-reduction is achievable pharmacologically by the combination therapy with $β_2$-AR agonist and CGRP when delivered relatively late after MI or at reperfusion.

Methods and Results: Terbutaline at the doses of 10 ng/kg, 100 ng/kg, and 1 mg/kg (in 0.5 ml saline) was IV infused respectively to 3 groups of rats, 20 min before LAD occlusion. This determined the dose-dependent effects of terbutaline on infarct size and its side effects on hemodynamics. CGRP 10 ng/kg was IV infused to another group of rats 20-min before LAD occlusion. The dosage of CGRP 10 ng/kg was based on previously determined one in rat MI model (Wolfram et al., 2005). The effects of terbutaline 10 ng/kg or CGRP 10 ng/kg on infarct size were further tested in the presence of $β_2$-AR and CGRP-receptor antagonists, respectively, with ICI-118,551(100 μg/kg/min) and $CGRP_{8-37}$ (3 ng/kg/min) Saline (0.5 ml) will be infused to rats serving as control.

Inventors used rat MI model (30-min ischemia and 4 h reperfusion). Pre-ischemic infusion (10-min) of the $β_2$-AR blocker ICI-118551 (100 μg/kg/min), CGRP-receptor blocker $CGRP_{8-37}$ (3 ng/kg/min), or their combination to the rats increased IS by 44%, 36%, and 72%, respectively (p<0.01, n=8/group). The $β_2$-AR agonist terbutaline (100 μg/kg/min) and CGRP (3 ng/kg/min) which were co-infused from the last 5-min of ischemia to the first 5-min of reperfusion reduced IS by 74% (p<0.01, n=4/group). CGRP or terbutaline alone did not reduce IS. The effect of combination therapy on myocyte protection was further assessed in a simulated ischemia-reperfusion model of isolated rat ventricular myocytes (2-hr ischemia and 1-hr reperfusion). Compared with saline control, the application of CGRP (1 nmol/L)+ terbutaline (100 nmol/L) at 30- and 60-min after ischemia reduced cell death by 11% and 9% (p<0.01) respectively. CGRP or terbutaline alone exerted no myocyte survival benefit. The mechanisms underlying combination therapy were determined by assessing myocardial PKA and PKC activity in normal rats. Infusion of CGRP, terbutaline or their combination, PKA activity increased by 10%, 30% and 80% peaked at 5-min post-infusion. (FIG. 1) In comparison, PKC activity (assessed by PKC translocation) was unchanged in the first 5-min of the drug infusion.

Conclusions: endogenous stimulation of CGRP-receptor and $\beta_2$-AR confers synergistic IS reduction. This protection can be achieved by combination therapy with $\beta_2$-AR agonist and CGRP delivered in the late phase of ischemia/early phase of reperfusion. Our findings provide a basis for novel pharmacological ischemic post-conditioning with therapeutic potential to reduce reperfusion injury in patients with acute MI.

Example 2

Post-Infarction Therapy with PKA Activation and $\beta$1-Adrenergic Receptor Blockade Confers Infarct-Size Reduction In Vivo Experimental Myocardial Ischemia-Reperfusion Model. The rat myocardial ischemia-reperfusion model will be used (Birnbaum et al., 2005; Huang et al., 2007a). This model consists of 30 min coronary artery occlusion followed by 4-hr reperfusion.

Protocol 1: To demonstrate the effect of PKA activator on infarct size reduction, a known PKA activator, milrinone (5 µg/kg/min) will be intravenously infused to rats starting at the last 5-minute of 30-minute ischemia to the first 5-minute of 4-hour reperfusion. To determine the effect of $\beta$1-adrenergic receptor antagonist and the synergistic action of both PKA activator and $\beta$1-adrenergic receptor antagonist, esmolol (10 g/kg/min) will be intravenously infused to rats with or without milrinone. Arterial blood pressure and heart rate will be monitored continuously throughout the experiments.

Method for in vivo myocardial infarct study: Following anesthesia and ventilation support, the chest is opened and the left coronary artery encircled with a suture and ligated for 30 min. The snare is then released and myocardium reperfused for 4 hr. The left coronary artery is then reoccluded and Evan's blue dye injected into the right ventricle. The LV is sliced into 6-7 sections. Tissue slices are incubated for 10 min in 1% 2,3,5-triphenyl-tetrazolium-chloride (TTC), fixed in 10% formaldehyde, and photographed to identify the ischemic myocardium at risk (uncolored by the blue dye), the necrotic zone (unstained by TTC) and the nonischemic zones (colored by blue dye). The areas of ischemia and necrosis in each slice are determined by planimetry, converted into percentages of the whole for each slice, and multiplied by the weight of the slice.

Figure 2:
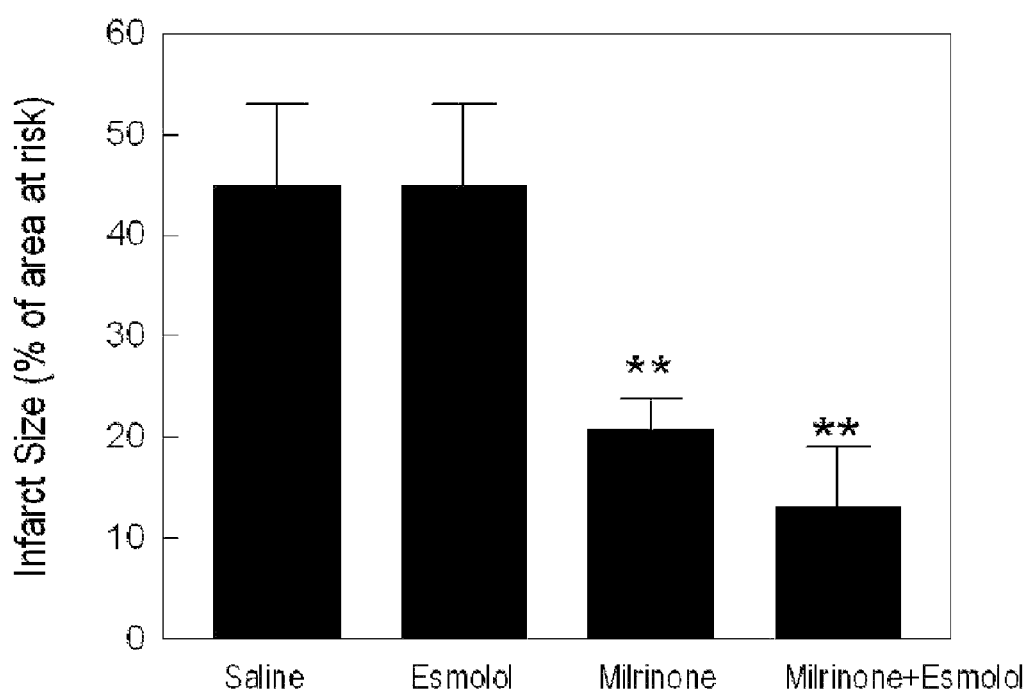
FIG. 2 Infarct-size reduction conferred by esmolol (10 μg/kg/min for 10-minute infusion), milrinone (5 μg/kg/min for 10-minute infusion), and co-infusion of milrinone and esmolol (10-minute infusion) all started at the last 5 minutes of 30-minute ischemia to the first 5 minutes of four-hour reperfusion. Compared with saline control, 53±5% ($p<0.01$), and 69±16% ($p<0.01$) infarct-size reduction is seen in the rats receiving milrinone, and the composition of milrinone and esmolol, respectively. Compared with saline, esmolol did not change infarct size. The infarct-size shows additional 41% reduction in rats receiving milrinone and esmolol compared to that with milrinone alone. N=6 rats/group. NS: not significant; **: $p<0.01$.
Figures 3A, 3B:
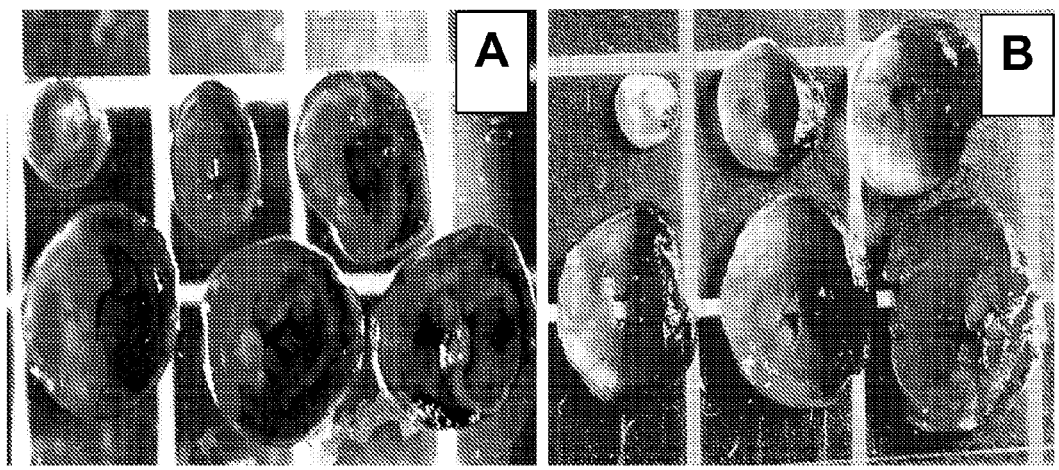
FIGS. 3A-3B Photo (FIG. 3A) shows a typical case of reduced infarct-size in a rat receiving milirinone and esmolol compared to a rat receiving saline infusion (FIG. 3B). Yellow zone within the red is the infarcted area. Red zone is the area-at-risk supplied by the occluded left anterior descending coronary artery. Blue zone is non-risk zone supplied by no-occluded right and circumflex coronary arteries. Infarct size is normalized as the ration of yellow-area/red-area. Acute infarction-reperfusion model consists of 30-minute occlusion of the left anterior descending coronary artery followed by four-hour reperfusion. Infarct-size was quantified at the end of four-hour reperfusion. N=6 rats/group.

The inventors have demonstrated that activation of PKA at late ischemia-early reperfusion phase confers infarct-size limiting effect. Administration of the phosphodiesterase inhibitor milrinone at late ischemia-early reperfusion phase confers robust infarct-size reduction in the rat ischemia/reperfusion model in vivo. (FIG. 2) Furthermore, the inventors have demonstrated that the combination therapy with milrinone and the selective $\beta_1$-adrenergic receptor antagonist esmolol confers incremental infarct-size limiting effect. (FIGS. 3A-3B)

Example 3

PKA Activation Confers Myocyte Protection Against Ischemia/Reperfusion In Vitro

To verify that infarct-size reducing or limiting effect is a direct product of PKA activation on myocyte survival but not a secondary effect due to salutatory coronary/systemic hemodynamic alternations, the inventors tested the effect of PKA activation by milrinone on isolated rat ventricular myocytes in primary culture. In vitro myocyte ischemia-reperfusion study consists of 2-hour hypoxia followed by 1-hour re-oxygenation. Hypoxia is created by layering mineral oil over the cells. Re-oxygenation is made by removal of the oil. Myocyte death is quantified at the end of 1-hour reperfusion.

Figure 4:
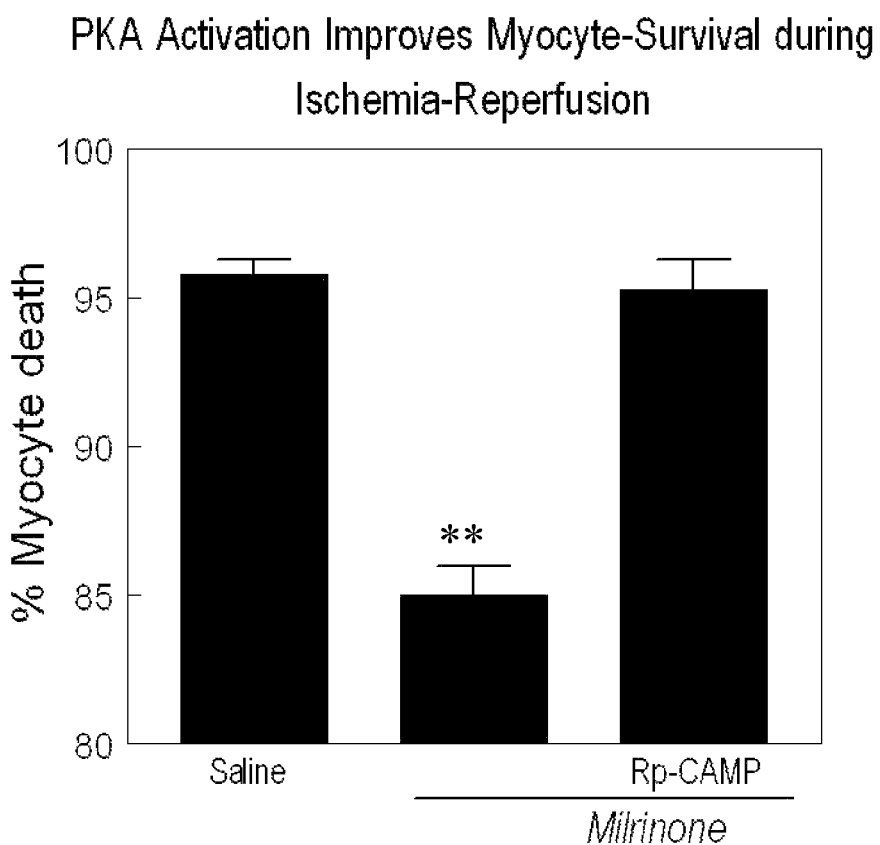
FIG. 4 Thirty minutes after the onset of ischemia, administration of milrinone (4.7 μmol/L) to ventricular myocytes reduces myocute death by 11% compared to saline control. The milrinone-induced myocyte protection is abolished in those cells pretreated with the PKA inhibitor Rp-CAMP (100 μmol/L). In vitro myocyte ischemia/reperfusion study consists of 2-hour hypoxia followed by 1-hour re-oxygenation. Hypoxia is created by layering mineral oil over the cells. Re-oxygenation is made by removal of the oil. Myocyte death is quantified at the end of 1-hour reperfusion. (Huang, 2007b). **: $p<0.01$.

The inventors have shown that activation of PKA by milrinone significantly reduces myocyte death by 11%, compared with the saline control. Milrinone induced cell protection against ischemia reperfusion is abolished in the presence of PKA inhibition (Rp-CAMP 100 µmol/L). (FIG. 4)

References

The following references, to the extent that they provide exemplary procedural or other details supplementary to those set forth herein, are specifically incorporated herein by reference.

U.S. Pat. No. 5,466,468
2004 NHLBI Chartbook
Almquist et al. *J. Med. Chem.*, 23:1392-1398, 1980.
Anand et al., *J. Am. Coll. Cardiol.*, 17:208-217, 1991.
Anonymous, *Am. J. Cardiol.*, 57:28F-33F, 1986.
Birnbaum et al., *Cardiovasc. Res.*, 65:345-355, 2005.
Brain and Grant, *Physiol. Rev.*, 84:903-934, 2004.
Cai et al., *Circulation*, 108(1):79-85, 2003.
Campbell et al., *Am. J. Cardiol.*, 60:422-423, 1987.
Chow et al., *Br. Heart J.*, 69:430-435, 1993.
Dubois-Rande et al., *Am. J. Cardiol.*, 70:906-912, 1992.
Ellis et al., *Circulation*, 104:2685-2688, 2001.
EP 45665
Felker et al., *J. Am. Coll. of Cardiol.*, 41:997-1003, 2003.
Freireich et al., *Cancer Chemother. Rep.*, 50:219, 1966.
Gennari et al., *Cardiovasc. Res.*, 24:239-241, 1990.
Gulbenkian et al., *Circ. Res.*, 73:579-588, 1993.
Hann, *J. Chem. Soc. Perkin Trans.*, I 307-314, 1982.
Hasbak et al., *J. Pharmacol. Exp. Ther.*, 304:326-333, 2003.
Heber et al., *Eur. Heart J.*, 8:11-18, 1987.
Holladay et al., *Tetrahedron. Lett.*, 24:4401-4404, 1983.
Hruby, *Life Sci.*, 31:189-199, 1982.
Huang et al., Circ Res, 2007a
Huang et al., *Am. J. Physiol.*, 276:R259-R264, 1999.
Huang et al., *Am. J. Physiol. Heart Circ. Physiol.*, 293:H376-H384, 2007b.
Hudson et al., *Int. J. Pept. Prot. Res.*, 14:177-185, 1979.
International Application No. PCT/US2008/062026.
Jennings-White et al., *Tetrahedron Lett.*, 23:2533, 1982.
Kudoh et al., *J. Cardiovasc. Pharmacol.*, 6:1201-1209, 1984.
Lefrak et al., *Cancer*, 32:302-314, 1973.
Lipsic et al., *J Am Coll Cardiol.*, 48(11):2161-7, 2006.
Lu et al., *Clin. Exper. Pharmacol. Physiol.*, 28:392-396, 2001.
Lundman et al., *Circuation*, 84:1993-2000, 1991.
Luo et al., *Eur. J. Pharmacol.*, 502:135-41, 2004.
Miyauchi et al., *Biochem. Biophys. Res. Commun.*, 155:289-294, 1988.
Morley, *Trends Pharm. Sci.*, 463-468, 1980.
Murry et al., *Circulation*, 74:1124-1136, 1986.
Packer et al., *N. Engl. J. Med.*, 325:1468-75, 1991.
Remington's Pharmaceutical Sciences" 15th Edition, pages 1035-1038 and 1570-1580, 1990.
Rizo and Gierasch, *Ann. Rev. Biochem.*, 61:387, 1992.
Roque et al., *Circulation*, 76:610-617, 1987.
Rude et al., *Am. J. Cardiol.*, 57:38F-42F, 1986.
Sanada et al., *Circulation*, 104:705-710, 2001.

Saetrum et al., *Eur. J. Pharmacol.*, 397:373-382, 2000.
Scientific Tables, Geigy Pharmaceuticals, Ardley, N.Y., 537, 1970.
Shekhar et al., *Am. J. Cardiol.*, 67:732-736, 1991.
Spatola et al., *Life Sci.*, 38:1243-1249, 1986.
Spatola, In: *Peptide Backbone Modifications*, 1:3, 1983a.
Spatola, In: *Chemistry and Biochemistry of Amino Acids, Peptides, and Proteins*, Weinstein (Ed.), Marcel Dekker, NY, 267, 1983b.
Staat et al., *Circulation*, 112:2143-2148, 2005.
Sueur et al., *J. Mol. Cell. Cardiol.*, 39:955-963, 2005.
Tokudome et al., *Endocrinology*, 143:3515-3521, 2002.
Uren et al., *Cardiovasc. Res.*, 27:1477-1481, 1993.
Van de Werf et al., *J. Am. Coll. Cardiol.*, 22:407-416, 1993.
Van Gelderen et al., *Eur. J. Pharmacol.*, 284:51-60, 1995.
Vinten-Johansen et al., *Circulation*, 112:2085-2088, 2005.
Wolfrum et al., *Regul. Pept.*, 127:217-224, 2005.

The invention claimed is:

1. A method of treating reperfusion or resuscitation injury in an individual comprising the step of: administering to an individual during or after reperfusion with an effective amount of a small molecule phosphodiesterase III (PDE III) inhibitor and a small molecule $\beta 1$-adrenergic receptor antagonist, wherein reperfusion injury to an ischemic tissue is reduced.

2. The method of claim 1, wherein the phosphodiesterase inhibitor is milrinone, or enoximone.

3. The method of claim 2, wherein the phosphodiesterase inhibitor is milrinone.

4. The method of claim 1, wherein the $\beta 1$-adrenergic receptor antagonist is acebutolol, atenolol, betaxolol, bisoprolol, esmolol, metoprolol, or nebivolol.

5. The method of claim 1, wherein the $\beta 1$-adrenergic receptor antagonist is esmolol.

6. The method claim 1, wherein reperfusion is after a myocardial infarction or cardiac arrest.

7. The method of claim 1, wherein the phosphodiesterase inhibitor is milrinone and the $\beta 1$-adrenergic receptor antagonist is esmolol.

8. The method of claim 1, wherein reperfusion is mechanical reperfusion or chemical reperfusion.

* * * * *